United States Patent [19]

Toth et al.

[11] Patent Number: 4,914,021

[45] Date of Patent: Apr. 3, 1990

[54] CARCINOMA OROSOMUCOID-RELATED ANTIGEN, A MONOCLONAL ANTIBODY THERETO, AND THEIR USES

[75] Inventors: Carol A. Toth, Westwood; Peter Thomas, Pembroke, both of Mass.

[73] Assignee: New England Deaconess Hospital Corporation, Boston, Mass.

[21] Appl. No.: 164,071

[22] Filed: Mar. 4, 1988

[51] Int. Cl.[4] ................... G01N 33/53; G01N 33/577; A61K 39/00; C07K 15/14
[52] U.S. Cl. .......................................... 435/7; 424/9; 424/85.8; 435/172.8; 435/240.27; 435/810; 436/501; 436/512; 436/548; 436/808; 436/813; 530/387; 530/395; 935/107; 935/108; 935/110
[58] Field of Search ................... 435/7, 172.2, 240.27, 435/810; 436/501, 548, 813, 512, 64, 808; 530/387, 395, 413, 828; 935/107, 108, 110, 103; 424/85, 9

[56] References Cited

U.S. PATENT DOCUMENTS

| | | | |
|---|---|---|---|
| 4,489,167 | 12/1984 | Ochi et al. | 436/518 |
| 4,612,121 | 9/1986 | Hermansson | 210/635 |
| 4,687,734 | 8/1987 | Chester | 435/7 |
| 4,708,930 | 11/1987 | Kortright et al. | 435/7 |
| 4,783,420 | 11/1988 | DelVillano et al. | 436/548 |

FOREIGN PATENT DOCUMENTS

| | | | |
|---|---|---|---|
| 0098162 | 1/1984 | European Pat. Off. | 436/548 |
| 0199196 | 10/1986 | European Pat. Off. . | |
| 0252200 | 12/1987 | Fed. Rep. of Germany | 436/548 |
| 8101409 | 5/1981 | World Int. Prop. O. | 436/548 |
| 8704183 | 7/1987 | World Int. Prop. O. . | |

OTHER PUBLICATIONS

Hayes et al., J. of Clinical Oncology, vol. 4 (10), Oct. 1986, pp. 1542–1550.
Khoo et al., Aust. and N.Z. Journal of Obstetrics and Gynaecology, vol. 22, 1982, pp. 65–70.
Ura et al., Cancer Letters, vol. 25, 1985, pp. 283–295.
Zamcheck et al., Cancer, vol. 47, 1981, pp. 1620–1627.
Paone et al., J. of Surgical Research, vol. 31, 1981, pp. 269–273.
Asaimoto et al., Anticancer Research, vol. 9, 1989, pp. 319–326.
Hansen et al., Cancer, vol. 60, 1987, pp. 1630–1635.
Toth et al., Biological Abstracts, vol. 76151, Sep. 1, 1983, Abstract No. 32448.
Hansen et al., Chemical Abstracts, vol. 104, 1986, Abstract No. 222908y.
Krupey et al., (1972), Biochem. 9:617–622.
Toth et al., (1985), Cancer Research, 45:392–397.
Ziegler et al., (1982), Cancer Research, 42:1567–1573.
Fink et al., (1982), Cancer Research, 42:1574–1578.
Ochi et al., (1984), Clinica. Chemica. Acta, 138:9–19.
Rudman et al., (1972), Cancer Research, 32:1951–1959.
Toth et al., (1982), Biochem J., 204:377–381.
Ochi et al., (1982), Clinica. Chemica. Acta., 122:145–160.
Ochi et al., (1983), Cancer Letters, 20:173–182.
Ura et al., (1985), Cancer letters, 25:283–295.
Toth et al., (Jun. 1987), Am. Soc. Biol. Chemists, ab. no. 1110, p. 2116.
Toth et al., (1988), 1988 FASEB Abstract Form.
Ochi et al., (1982), Journal of Immunological Methods, 52:213–221.

*Primary Examiner*—David M. Naff
*Assistant Examiner*—Florina B. Hoffer
*Attorney, Agent, or Firm*—Lahive & Cockfield

[57] ABSTRACT

Disclosed is a glycoprotein, carcinoma orosomucoid-related antigen, (CORA), which has a binding affinity for carcinoembryonic antigen (CEA). This glycoprotein is a marker for carcinoma, and can be characterized by having a molecular weight of about 46,000–50,000 daltons, an isoelectric point of about 3.0–3.5, a carbohydrate content of about 25–35% by weight, reactivity with antisera raised thereto, and substantially no reactivity with antisera raised to nonspecific cross-reacting antigen (NCA) or to CEA. Also disclosed are a hybridoma which produces a monoclonal antibody to CORA, the monoclonal antibody to CORA, and a device, kit, and method for detecting and monitoring carcinoma.

15 Claims, 4 Drawing Sheets

4,914,021

CARCINOMA OROSOMUCOID-RELATED ANTIGEN, A MONOCLONAL ANTIBODY THERETO, AND THEIR USES

BACKGROUND OF THE INVENTION

The U.S. Government has rights in this invention pursuant to the National Institutes of Health Grant Nos. CA 44583 and CA 44704.

The present invention relates to the field of cancer diagnosis, and more specifically to the identification of new methods and cancer markers useful in the diagnosis, detection, and monitoring of human colorectal carcinoma.

Colorectal adenocarcinoma is a cancer which affects many people per year. The prognosis is poor in about 50% of the cases because the tumor is often not detected until the disease has spread and has reached a terminal stage. Early diagnosis is important to increase chances of arresting the carcinoma before it metastasizes, thereby leading to an improved prognosis.

One method of tumor diagnosis is detection of the presence of acute-phase reactant proteins, the levels of which increase in the blood in the presence of a malignant disease. Alpha-1-acid glycoprotein (AGP) is such a protein, and accordingly, has been utilized as an indicator of such malignant diseases as colorectal adenocarcinoma.

A more specific method of early tumor diagnosis is detection of the presence of a marker or antigen specific for a particular type of tumor. These normally proteinaceous markers are synthesized by the tumor, and may be found in the serum, ascites fluid, and/or on the surface of the tumor. Only a limited number of tumor markers for colorectal carcinoma have thus far been found to have clinical use. These include carcinoembryonic antigen (CEA), nonspecific cross-reacting antigen (NCA), and the sialylated Lewis A antigen (CA 19.9).

CEA in particular appears in elevated amount in patients with a variety of cancers including colorectal adenocarcinoma. It is a glycoprotein having a molecular weight of approximately 180,000 daltons. CEA contains complex oligosaccharide chains which comprise over fifty percent of the molecule by weight, and which are composed of fucose, sialic acid, N-acetyl glucosamine, galactose, and mannose. Once elicited by the tumor, circulating CEA is cleared and metabolized by the liver.

Patients whose condition has been accurately diagnosed as colorectal adenocarcinoma have demonstrated a broad range of circulating CEA levels. For example, approximately 40% of diagnosed patients have substantially no detectable CEA when initially examined. Unfortunately, there is no commercially available serodiagnostic marker which can be used to detect the tumor in these patients and to monitor therapy. On the other hand, patients with liver metastases, particularly when accompanied by underlying cholestasis, demonstrate very high CEA levels. This wide range has been attributed to many factors including (1) the rate of CEA production (which depends on tumor load, invasiveness, vascularity, differentiation, and sites of metastases), and (2) the rates of clearance and metabolism of CEA.

A recent study by the present inventors has determined that patients with high plasma CEA values may have a variant form of CEA which is cleared from the circulation by the human liver or by cultured rat Kupffer cells much more slowly than other forms of CEA. The slower rate of CEA clearance has been hypothesized to enhance the probability of CEA detection by various assays or screening procedures, therefore making it a desirable characteristic.

To determine why seemingly different forms of CEA are cleared at different rates would aid in the development of new or improved methods of carcinoma detection, identification, and monitoring. Moreover, a better understanding of the physical characteristics of the protein moiety which is recognized by the Kupffer cell CEA receptors may also lead to improved treatments for carcinomas such as colorectal adenocarcinoma. In addition, there will always exist a need to find new markers for cancers which thus far have none, such as some forms of undifferentiated or poorly differentiated colorectal adenocarcinoma and for new therapeutic methods.

Accordingly, it is an object of the present invention to identify the physical features which distinguish fast clearing CEA from slow clearing CEA.

It is another object of the present invention to provide a new cancer marker for the detection, diagnosis, and monitoring of carcinoma, and in particular, of colorectal adenocarcinoma.

Yet another object of the invention is to provide an antibody which recognizes the new cancer marker, thereby enabling the detection of carcinoma cells, and in particular, of colorectal adenocarcinoma cells.

A further object of the present invention is to provide a method of detecting and monitoring the treatment of a previously undetectable carcinoma.

SUMMARY OF THE INVENTION

A new tumor marker for carcinoma has been discovered which has a binding affinity for CEA, and which, when bonded to CEA, retards CEA clearance from the circulation of a subject by the liver. This marker is carcinoma orosomucoid-related antigen, (hereinafter referred to as "CORA"), a glycoprotein which can be isolated from the ascites fluid of patients with colorectal adenocarcinoma.

CORA has a molecular weight in the range of of approximately 46,000–50,000 daltons, and has a heterogenous acidic isoelectric point of between 3.0 and 3.5. It has substantially no cross-reactivity with polyclonal antisera raised to NCA or to CEA.

Carbohydrate analysis of CORA reveals that about 25–35% of the molecule by weight is composed of oligosaccharide. The oligosaccharide species in a common form of CORA having about 30% by weight carbohydrate comprise approximately 0.2% fucose, approximately 10.3% N-acetyl glucosamine, and approximately 5.9% sialic acid.

CORA's binding affinity for CEA makes it useful as part of a device for assay or purification purposes. Such a device comprises a support to which at least a portion of the glycoprotein is bound.

A monoclonal antibody which reacts with CORA, and which will not cross-react with AGP has been produced by a hybridoma. The antibody is useful in detecting, diagnosing and monitoring carcinoma. The eliciting hybridoma may be formed upon the fusion of a mouse myeloma cell, such as one from the NS-1 line, with a spleen cell from a mouse previously immunized with slow clearing CEA. The immunogen may alternatively be the CORA glycoprotein, or analogs or portions thereof.

A device useful for the assay or purification of CORA or of CORA bound to CEA has been developed which includes an anti-CORA antibody bound to a support. The antibody may be a monoclonal antibody which reacts with CORA.

CORA, as a tumor marker, is useful in detecting and diagnosing a plurality of carcinomas including colorectal adenocarcinoma. A label such as a radioactive isotope, enzyme, stable free radical, coenzyme, fluorescent group, chemiluminescent group, or colorimetric compound may be attached to CORA for labeling purposes.

Further, a kit for screening a patient for carcinoma, and in particular, colorectal adenocarcinoma, has been developed. This kit contains a plurality of different antisera specific for tumor markers including CORA, CEA, NCA, CA 19.9, and AGP.

A method for detecting and monitoring a carcinoma in vivo, and in particular, colorectal adenocarcinoma, has been developed which includes the use of CORA. In this method, the amount of CEA in the circulation of a subject is initially measured to establish a baseline level of CEA. A formulation comprising one of a group consisting of CORA, analogs, fragments and derivatives thereof which have a binding affinity for CEA is then administered to the circulation of the subject. The subject is then screened for an increase in the level of circulating CEA relative to the established baseline level. The CORA-containing formulation can be administered via injection. Both the measuring and screening steps can be accomplished by two additional steps including obtaining a specimen of a body fluid from the subject, and conducting an assay, and in particular, an immunoassay for CEA on that specimen. The body fluids useful for assay include whole blood, serum, and ascites fluid.

A method of detecting carcinoma cells has been developed. This method includes contacting a biological sample with an antibody or portion thereof which reacts with the CORA glycoprotein, analogs, or fragments thereof, but which does not cross-react with AGP, and observing if the antibody reacts with the sample. The biological sample may be whole blood, serum, ascites fluid, a tissue biopsy, a tumor, a tissue culture, or a histological preparation thereof. The antibody may be a monoclonal antibody, or fragment thereof which is capable of reacting with CORA. An immunoassay may be utilized to observe the extent of reaction between the antibody and the sample.

Another method has also been developed which enables the detection and monitoring of colorectal adenocarcinoma in a patient. In this method a biological sample is subjected to at least one of a plurality of tests, each of which indicates the presence of a particular cancer marker, and then the presence of that marker is then determined. The markers are selected from the group consisting of CORA, CEA, AGP, NCA, and CA 19.9. The test may be any type of assay, but preferably is an immunoassay which employs an antibody specific for a tumor marker. The tests may be carried out sequentially until one of them indicates the presence of a particular marker.

A method of localizing a carcinoma in vivo utilizing CORA has also been developed. This method includes administering to the circulation of a subject a formulation containing CORA, analogs, derivatives, or fragments thereof which have a binding affinity for CEA. Next, an antibody which reacts with CORA, and which has a label attached thereto is administered. The location of that antibody within the subject is then determined. The administering steps may be executed by injection. The antibody useful in this method is preferably a monoclonal antibody which reacts with CORA. The label attached to the antibody may be a radioactive isotope, enzyme, stable free radical, coenzyme, toxin, or a fluorescent, chemiluminescent, or colorimetric group.

Further, a method has been devised to retard the clearance of CEA from the circulation of a subject. This method is based on CORA's binding affinity for CEA, and that when bound to it, slows the rate of CEA metabolism by the liver. The method includes administering to the circulation of a subject a formulation containing CORA or an analog, derivative, or fragment thereof which has a binding affinity for CEA. The administered CORA will bind circulating CEA, thereby retarding CEA clearance and metabolism by the Kupffer cells of the liver. The CORA-containing formulation may be administered by injection.

BRIEF DESCRIPTION OF THE DRAWINGS

The foregoing and other objects of the present invention, the various features thereof, as well as the invention itself may be more fully understood from the following description, when read together with the accompanying drawings in which.

DESCRIPTION OF THE INVENTION

A new tumor marker for carcinoma, CORA, has been discovered which has a binding affinity for CEA, and which, when bonded to CEA, retards CEA clearance from the circulation of a subject by the liver. CORA, like CEA can be isolated from the ascites fluid of patients with colorectal adenocarcinoma.

Figure 1:
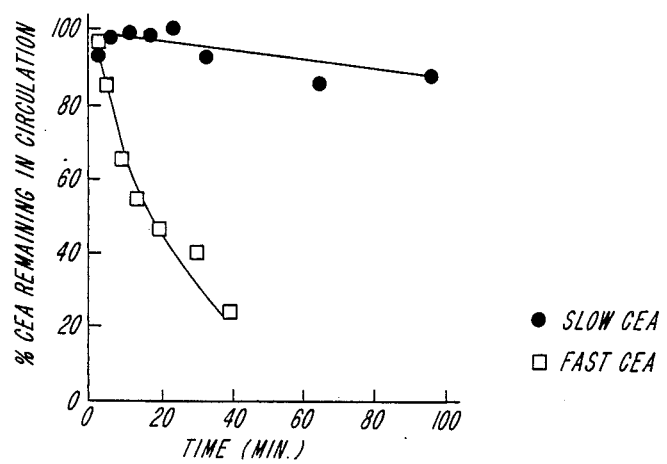
FIG. 1 is a graphic comparison of the circulatory clearance rates of fast and slow CEA from the in vivo circulation of the rat.

When CEA is purified from the malignant ascites fluid of certain patients with diagnosed colorectal adenocarcinoma, a CEA variant found in abnormally high levels in the plasma is detected. When this variant is injected into rats, it is cleared by the liver more slowly than other forms of CEA; hence the nomenclature "slow clearing", or "slow CEA" and "fast clearing", or "fast CEA". FIG. 1 shows that the systemic clearance rates of the two forms differ by a factor of about 5, with the $t_{\frac{1}{2}}$ of slow CEA being 15.1 minutes, while that of fast CEA being 3.1 minutes.

In addition, the two CEA species have different carbohydrate contents, high pressure liquid chromatography (HPLC) profiles, and isoelectric points.

However, both fast and slow species have reactivity in various immunoassays for CEA including, for example, radioimmunoassays (RIA) and enzyme-linked immunoabsorption assays (ELIZA). These assays employ antisera raised to CEA, and thus demonstrate a structural homology between the two species.

Both CEA preparations run as a single diffuse band of about 180 kD-200 kD molecular weight on nondenaturing slab gels. However, upon being subjected to sodium dodecyl sulfatepolyacrylamide gel electrophoresis (SDS-PAGE), slow CEA reveals an additional polypeptide having a molecular weight of about 46 kD-48 kD. This lower molecular weight polypeptide is also detected when CEA-active Sepharose CL-4B fractions of perchloric acid-extracted ascites fluid are subjected to further chromatography on Sephadex G-200.

Figure 3:
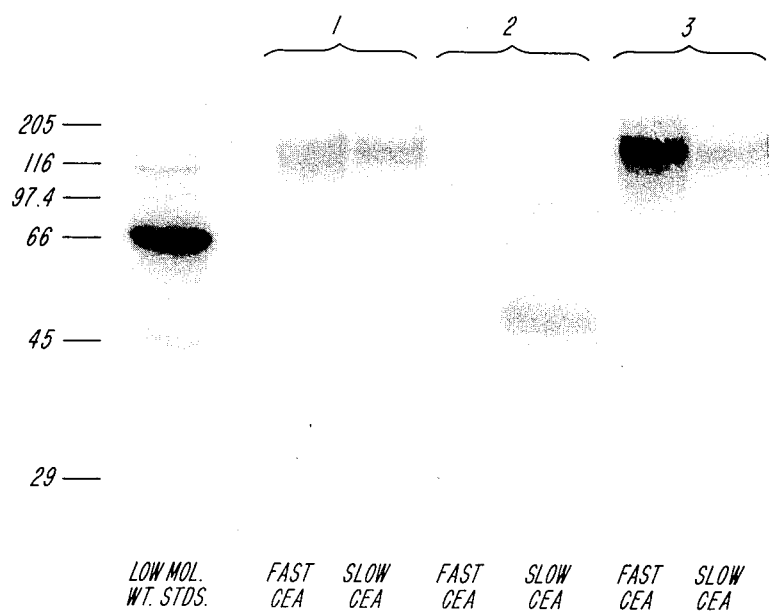
FIG. 3 is an autoradiogram of a Western transfer of fast and slow CEA probed with three antisera; (1) anti-CEA; (2) anti-AGP; (3) anti-NCA.

Immunological examination by Western blot analysis reveals that the 46 kD-48 kD protein cross-reacts with polyclonal antisera to AGP, but not to NCA (FIG. 3). Additional homology with AGP includes molecular weight and isoelectric point.

Figure 5:
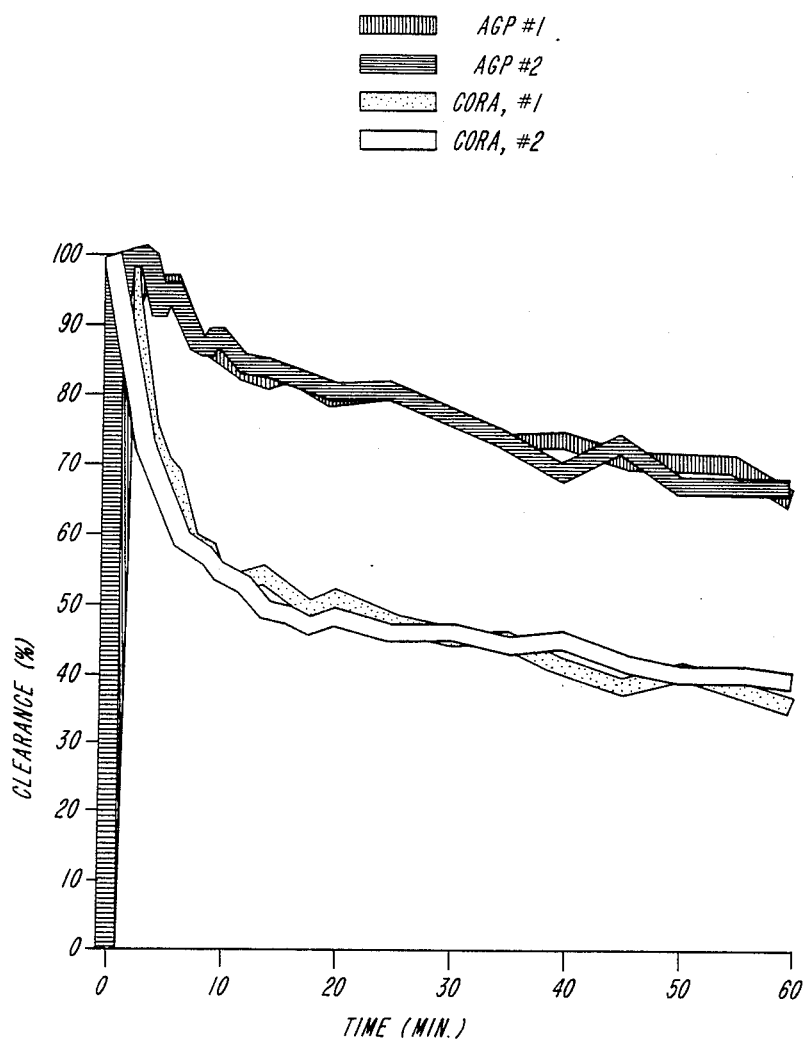
FIG. 5 is a graphic comparison of the in vivo clearance rates of CORA and AGP from the circulation of the rat liver.

However, CORA differs from AGP in the following ways:

(1) carbohydrate analysis of AGP and the 46K-48K protein demonstrates two different oligosaccharide profiles (see TABLE 1); AGP contains more sialic acid and total carbohydrate than does CORA;

(2) the pattern and rate of clearance of AGP and CORA from the circulation of the rat are quite different; CORA is removed in a biphasic manner with a rapid first phase ($t_{\frac{1}{2}}=10$ min) followed by a slower second phase ($t_{\frac{1}{2}}=$greater than 1 hr), while AGP has one clearance rate which is much slower ($t_{\frac{1}{2}}=$greater than 1 hr) (see FIG. 5);

(3) the effect which AGP and CORA have on the rate of CEA endocytosis by isolated rat liver Kupffer cells differs greatly; CORA retards it (FIG. 4), while AGP has no affect on it;

(4) amino acid analysis of CORA and AGP yield a distinctly different profiles (TABLE 2);

(5) circular dichroism analysis of CORA and AGP yield different secondary structures (TABLE 3); and (6) the responses of CORA and AGP to a monoclonal antisera raised to slow CEA are different; CORA reacts with it, while AGP has substantially no reactivity.

The above differences indicate that CORA and AGP are distinct proteins. The homology between AGP and CORA may be adventitious. Alternatively, CORA may be a member of the immunoglobulin "supergene" family, of which AGP and CEA are also members, and which implies some degree of sequence homology with these proteins as well as with immunoglobulins.

It has now been determined that slow CEA consists of CORA bound to CEA, and fast CEA consists of CEA with no or little CORA bound thereto. Slow CEA is slowly cleared between CORA retards CEA uptake by Kupffer cells of the liver. Slow CEA is retained in the circulation for a longer period of time than is fast CEA, thereby enhancing its probability of CEA detection, and allowing for more prompt therapeutic treatment of the carcinoma.

The physical properties of CORA, as well as its degree of purity after isolation have been determined by a number of analytical methods well known by those skilled in the art. These include immunonological recognition by, for example, an enzyme linked immunoabsorbant assay (ELISA), and dot blot and Western blot analyses; molecular weight determination by, for example, polyacrylamide gel electrophoresis (PAGE) and high pressure liquid chromatography (HPLC); secondary structure determinations by, for example, measurement of circular dichroism; separation techniques such as PAGE and HPLC; and carbohydrate and amino acid analyses by either manual or automated methods. Alternative techniques known to those skilled in the art could have been performed to determine most of these properties.

Because CEA is known to be metabolized by the rat liver, the rat was used as a model for in vivo circulatory clearance studies. These studies were carried out essentially as described by Toth et al. (Cancer Res. (1985) 45: 392-397), herein incorporated as reference. However, these studies could have been performed in alternative animal models such as the dog, rat, hamster, baboon, rabbit, or mouse might be used, since the liver of these species are also known to have CEA-clearing capabilities.

The first step in the hepatic metabolism of CEA is the endocytosis of CEA by Kupffer cells. Rat Kupffer cells therefore were isolated as described by Toth et al. (ibid.) to be utilized to study the molecular specificity of CEA binding, and the effects of CORA and AGP binding on the endocytosis of CEA.

A monoclonal antibody which reacts with CORA, and which does not cross-react with related proteins such as AGP, has been developed. Monoclonal antibodies or active fragments thereof which react with CORA, and which will not cross-react with AGP are generated by applying generally known cell fusion techniques (see, e.g., Kohler and Milstein (1976) E. J. Immunol. 6: 511-519; Shulman et al. (1978) Nature 276: 269-270) to obtain a hybridoma producing the antibody, and then by deriving a monoclonal antibody from the hybridoma. Slow CEA has been used as the initial innoculum. However, CORA may be used for the same purpose since the antibody is specific for CORA.

Alternatively, the antibody may be synthesized in whole or in part by biosynthetic or recombinant means. It may also consist of a fragment or modification of an antibody which is capable of reacting with CORA, such as a Fab fragment, and may have an additional group attached thereto, such as a marker, toxin, or biologically active molecule such as an enzyme or a second antibody.

The following example illustrates the preferred mode of making and practicing the present invention, but is not meant to limit the scope of the invention since alternative methods may be utilized to obtain similar results.

EXAMPLE

1. Purification of CORA

CORA was isolated from ascites fluids from patients with colorectal adenocarcinoma containing high levels of slow clearing CEA. The procedure employed was the method of Westwood and Thomas ((1975) Br. J. Cancer 32: 708-719) for CEA purification. An equal volume of cold (4° C.) 2.0M perchloric acid was added to the cold ascites fluid, and the mixture was stirred for 30 minutes at 4° C. The resulting suspension was centrifuged at 3,500×g for 20 minutes at 4° C. The sediment was discarded. The supernatant was dialyzed against cold running tap water for 48 hours and subsequently against frequent changes of deionized water (4° C.) until it reached neutral pH (7.0). The dialysate was centrifuged at 3,500×g for 20 minutes at 4° C., and the supernatant lyophilized.

Further purification was achieved by column chromatography. Phosphate buffered saline (PBS) with 0.01% sodium azide was the elution medium for the columns. The crude lyophilized extract was redissolved in PBS and applied to a Sepharose 4B column (10×100 cm). CORA-containing fractions were identified by an ELIZA and a dot blot assay for CEA as described below. The fractions were pooled and dialyzed against deionized water, and then lyophilized.

CORA appears in two distinct places during chromatography; with CEA as a complex; and at a larger elution volume as uncomplexed, free molecule.

Partially purified CORA dissolved in PBS was applied to a Sephadex G-200 column (5×100 cm). CORA not bound to CEA adsorbs to the column. The eluted fractions were assayed for activity as described above. Pooled CORA-containing fractions were dialyzed against deionized water.

2. Purification of CEA

CEA was obtained by the method of Westwood and Thomas (1975) as described above, except that liver metastases of colorectal adenocarcinoma obtained from autopsies, plasma samples, or ascites fluid taken from human subjects with diagnosed carcinomas were used as starting material.

3. Analytical Procedures

A. ELISA:

An ELISA for CEA was performed using the commercially available Roche immunoassay for CEA (Hoffman-LaRoche, Nutley, N.J.).

B. Dot Blot Assay:

Column fractions were analyzed for reactivity to polyclonal goat anti-CEA and rabbit anti-AGP antisera by dot blot assay. The samples (5 μl) were spotted on nitrocellulose membranes and probed with goat antisera to CEA and rabbit antisera to AGP. Reactions were visualized using either $^{125}$I-labeled rabbit anti-goat or goat anti-rabbit antisera.

C. HPLC:

Chromatography (HPLC) of fast and slow CEA on a TSK 4000 and 3000 gel filtration columns (Tyosoda) run in series reveals two species with 33 minute and 36 minute retention times, respectively. 30% of slow CEA is composed of the 33 minute peak, while only 7% of fast CEA is composed of that peak. These results imply that 33 minute peak size difference is due to the binding of CORA to CEA.

D. Western Blot Analysis:

Fast and slow clearing CEA were subjected to SDS-PAGE on 10% gels, and were electrophoretically transfered to nitrocellulose membranes according to the method of Towbin et al. ((1979) Proc. Natl. Acad. Sci. U.S.A. 76: 4350-4354). The nitrocellulose membranes were probed with goat anti-CEA and anti-NCA antisera, and rabbit anti-AGP antisera. Reactions were visualized using either $^{125}$I-labeled rabbit anti-goat antisera or a $^{125}$I-labeled goat anti-rabbit antisera.

The autoradiogram of such a transfer shown in FIG. 3 demonstrates that neither fast nor slow CEA are recognized by anti-AGP antisera, and that neither anti-NCA nor anti-CEA antisera recognize CORA. However, CORA is recognized by anti-AGP antisera.

E. Isoelectric Focusing:

CEA, CORA, and AGP were radioiodinated with $^{125}$I using the chloramine T procedure of Greenwood et al. ((1963) Biochem. J. 89: 114-123) to procure a specific radioactivity of about 6-10 mCi/mg. Focusing was carried out in agarose gels by the method of Saravis et al. ((1979) J. Immunological Methods 29: 91-96). Radiolabeled protein was detected by autoradiography using Kodak X-OMAT film.

These studies demonstrate that slow CEA consists of more species with lower isoelectric points than does fast CEA, thereby implying charge differences.

F. Carbohydrate Analysis:

Carbohydrate analyses of CEA, CORA, and AGP were carried out using the method of Reinhold et al. ((1972), Adv. Enzymol. 25: 244-249), at the Laboratory of Carbohydrate Research, The Massachusetts General Hospital, Boston, MA. The results of this analysis are shown in TABLE 1 below.

TABLE 1

CARBOHYDRATE ANALYSIS
SUGAR CONTENT OF GLYCOPROTEINS
(EXPRESSED AS % OF TOTAL CARBOHYDRATE)

| SUGAR | SLOW CEA | FAST CEA | CORA | AGP |
|---|---|---|---|---|
| Fucose | 5.7 | 18.8 | 0.7 | 0.5 |
| Mannose | 15.0 | 15.3 | 17.6 | 14.5 |
| GALACTOSE | 22.5 | 19.3 | 26.4 | 20.0 |
| GLUCOSE | 0 | 0.3 | 0 | 0 |
| GLUCNAC | 36.4 | 38.3 | 34.8 | 34.8 |
| SIALIC ACID | 20.4 | 8.2 | 19.9 | 28.7 |
| TOTAL CARBOHYDRATE | 40% | 50% | 30% | 45% |

As shown above, slow CEA has a higher ratio of sialic acid to fucose than fast CEA.

H. Amino Acid Analysis:

Amino acid analysis was performed using the Pico Tag ™ Amino Acid Analysis System (Waters Div., Millipore Corp.). The method involves the reaction between the amino acid and a derivatizing reagent prior to separation with a reverse phase HPLC column, and then detection with UV at 254 nm.

The results are shown in TABLE 2.

TABLE 2

| AMINO ACID ANALYSIS (mole %) | | | |
|---|---|---|---|
| AMINO ACID | CORA | AGP | CEA |
| Ala | 4.4 | 3.0 | 6.2 |
| Arg | 4.3 | 5.8 | 3.5 |
| Asx | 18.2 | 11.2 | 14.6 |
| Cys | 1.0 | 1.9 | 1.6 |
| Glx | 12.0 | 17.9 | 10.3 |
| His | 4.1 | 1.9 | 2.2 |
| Ileu | 3.4 | 5.3 | 4.2 |
| Leu | 9.3 | 7.4 | 8.4 |
| Lys | 2.6 | 8.4 | 3.0 |
| Met | 0 | 0.6 | 0 |
| Phe | 6.3 | 6.2 | 2.4 |
| Pro | 5.6 | 3.2 | 8.3 |
| Ser | 11.1 | 2.4 | 10.9 |
| Thr | 3.0 | 7.5 | 9.6 |
| Try | N.D. | 2.6 | N.D. |
| Tyr | 6.9 | 8.4 | 3.3 |
| Val | 3.0 | 4.2 | 7.0 |

H. Circular Dichroism Analysis:

Secondary protein structure was determined by circular dichroism measurements on a AVIV Circular Dichroism Spectropolarimeter, MODEL 60. DS, and the resulting data was analyzed according to the method of Yang, et al. (1986), "Calculation of Protein Conformation from Circular Dichroism" in *Methods in Enzymology* vol. 130 pp. 208). TABLE 3 compares the secondary structure of CORA, fast and slow CEA, and AGP.

TABLE 3

| STRUCTURE | CORA | FAST CEA | SLOW CEA | AGP |
|---|---|---|---|---|
| Alpha Helix | 17.0% | 0.0% | 14.4% | 10.1% |
| Beta Sheet | 35.3% | 82.2% | 49.7% | 55.4% |
| Beta Turn | 18.8% | 3.1% | 14.1% | 12.1% |
| Random Coil | 28.9% | 14.6% | 21.7% | 22.4% |

CORA's structure is composed of more alpha helix, beta turn, and random coil than are those of fast CEA and AGP. Slow CEA has alpha helix due to CORA being bound to the molecule.

4. Circulatory Clearance Studies

The rates of circulatory clearance of fast and slow clearing CEA by the rat liver were determined as follows. Rats were anesthetized with sodium pentabarbital (50 mg/kg) given intraperitoneally. Sufficient CEA either purified and dissolved in saline or unpurified and present in patient's unextracted serum, was injected in the femoral vein of male Sprague-Dawley rats to yield an initial plasma concentration of 750 ng/ml. Blood (20 ul) was collected from the tail vein at one minute intervals to the end of an hour. The blood samples were pipetted directly into 1 ml of 0.037M EDTA buffer (pH 7.6) containing 0.02% bovine serum albumin. The samples were assayed in duplicate for CEA content using an ELIZA. Clearance rates of $^{125}$I-labeled CEA were determined by the same procedure except that the CEA content of the blood samples was measured directly in a Packard autogamma counter. The results shown in FIG. 1 clearly demonstrate two distinct rates of clearance.

The rates of circulatory clearance of CORA and AGP were determined in a similar manner. The results shown in FIG. 5 demonstrate that CORA is removed from the circulation of the rate by the liver in a biphasic manner; the first phase is rapid ($t_{\frac{1}{2}} = 10$ min) and mediated by the liver. Alpha$_1$ acid glycoprotein has a long circulatory half life (greater than one hr).

5. Kupffer Cell Isolation

Kupffer cells were isolated according to the method of Toth et al. (ibid.). Cells were harvested from the livers of anesthetized male Sprague-Dawley rats (250–300 g) by collagenase digestion, differential centrifugation and final purification on a (17.5%) metrizamide gradient. Greater than ninety-five percent of the resulting sinusiodal cells were viable by trypan blue dye exclusion. Sixty-five percent of the cells were macrophages by nonspecific esterase staining and sixty-four percent of the cells phagocytosed collodial carbon. The preparation contained less than 1% hepatocytes, as counted microscopically.

6. Endocytosis of CEA in vitro by Kupffer Cells

CEA endocytosis by Kupffer cells was monitored using a cell suspension assay with $I^{125}$-radiolabeled CEA. Kupffer cell suspensions were incubated with identical concentrations of different radiolabeled CEA preparations with and without added CORA. CEA uptake by the isolated cells at 37° C. was measured at several time points up to one hour and compared.

Figure 2:
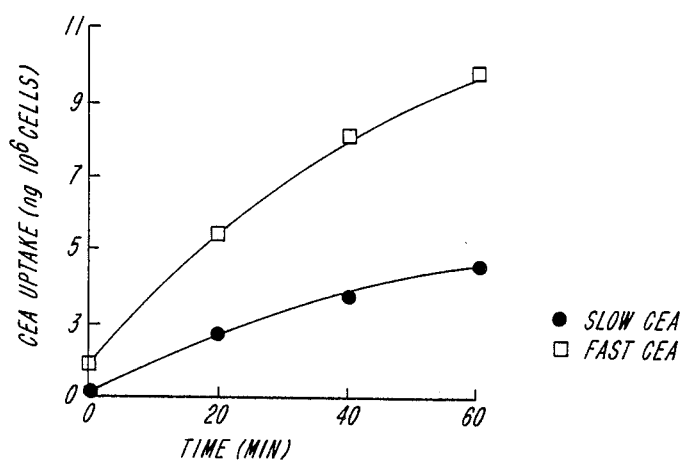
FIG. 2 is a graphic comparison of the in vitro uptake of fast and slow CEA by rat liver Kupffer cells.
Figure 4:
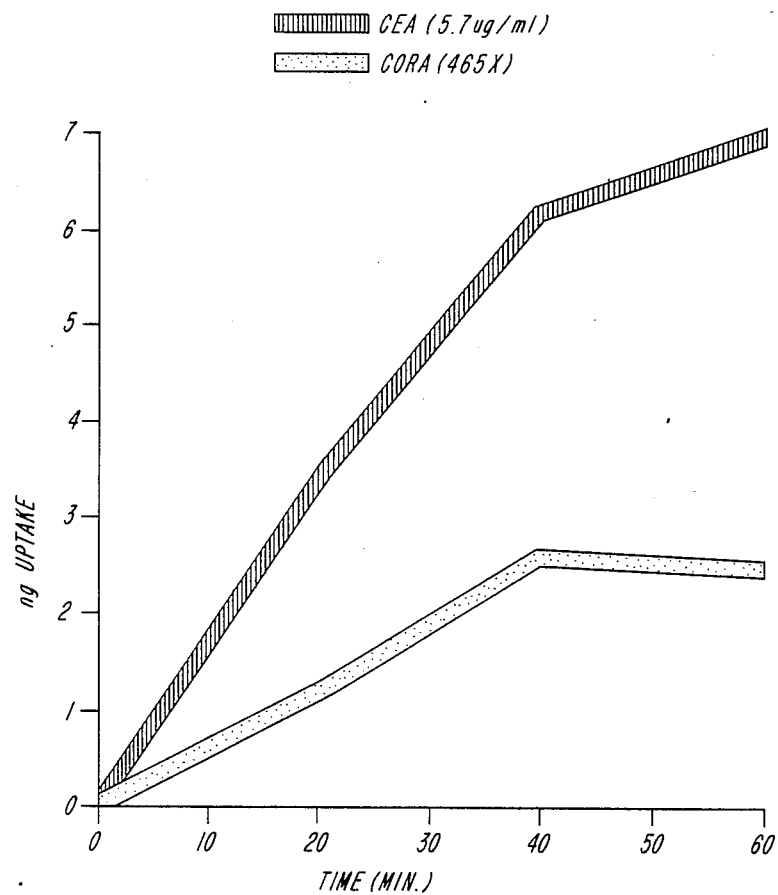
FIG. 4 is a graphic comparison of the in vitro uptake of CEA by rat liver Kupffer cells in the presence and absence of CORA.

FIG. 2 demonstrates that slow CEA is endocytosed at a slower rate than fast CEA, and FIG. 4 shows that CORA inhibits CEA clearance by reducing the rate of endocytosis by isolated rat liver Kupffer cells.

7. Hybridoma and Monoclonal Antibody Production

Balb/c mice (The Jackson Laboratory, Bar Harbor, Me; 6–8 weeks old) were immunized with 4 injections of slow CEA obtained from the ascites fluid of a patient with diagnosed colorectal adenocarcinoma. The injections were performed weeks apart and 100 μg was injected on each occasion. The first 3 injections were given intraperitoneally, and the last intravenously. Slow CEA was injected with complete Freunds adjuvant on the first occasion, incomplete adjuvant on the second and third occasions, and without adjuvant on the last occasion. Serum withdrawn prior to the last injection showed prominent binding to both the immunogen and purified CORA using a solid phase microtiter plate enzyme-linked immunoassay. The mouse with the best immune response was sacrificed three days after the last injection.

Hybridomas were produced fusion of spleen cells from the sacrificed mouse with NS-1 (P3NS-1/1-Ag4-1) myeloma cells (American Type Culture Collection, Rockville, MD.; Acc. No. TIB18). In the present example, the method of Nadakavukaren ((1984) (*Differentiation* 27: 209-202) was employed to perform the fusions. Resultant clones were tested for binding to slow CEA, CORA, and AGP in a solid phase ELISA. Subcloning by serial dilution was carried out twice on the 9C2 clone which bound to slow CEA and CORA, but not to AGP. The most productive subclone was injected into the peritoneal cavity of Balb/c mice to produce ascites fluid containing monoclonal antibody. The hybridoma which produces this subclone was deposited with the American Type Culture Collection (Rockville, MD.; Acc. No. HB9650) on 3/23/88. The ascites fluid obtained was centrifuged, tested for activity, and then stored at −70° C. until required. This source of monoclonal antibody, designated "ND5" or "anti-CORA", was used in all subsequent investigations.

8. Characterization of Resulting Monoclonal Antibodies

The anti-CORA ND5 antibody was screened to determine isotype by the Ouchterlony double diffusion test (Ouchterlony et al. (1978) in *Handbook of Experimental Immunology* (3rd ed.), Blackwell Scientific Publication, London, vol. 1, pp. 19.1–19.40) in agar plates against anti-IgM, anti-IgG, anti-IgG$_1$, anti-IgG$_{2a}$, anti-IgG$_{2b}$, and anti-IgG$_3$ antibodies (Cappell Laboratories). Precipitating bands were produced only with anti-IgG and anti-IgG$_1$ antibodies.

The present invention may be embodied in other specific forms without departing from the spirit and scope thereof. Accordingly, other embodiments are within the following claims.

We claim:

1. A monoclonal antibody specific to carcinoma orosumucoid-related antigen (CORA) glycoprotein,
    said CORA glycoprotein having a binding affinity for the tumor marker carcinoembryonic antigen (CEA), having a molecular weight of about 46,000–50,000 daltons, an isoelectric point in the range of about 3.0–3.5, a carbohydrate content of about 30% by weight, of which approximately 10.3% is N-acetyl glycosamine and approximately 0.2% is fucose, and having substantially no cross-reactivity with antisera to nonspecific cross-reacting antigen (NCA) or to CEA.

2. The monoclonal antibody of claim 1 wherein said antibody has substantially no cross-reactivity with alpha-1-acid glycoprotein (AGP).

3. The monoclonal antibody of claim 1 wherein said antibody is produced by a hybridoma, said hybridoma being a fusion product of a mouse myeloma cell and a spleen cell from a mouse previously immunized with slow clearing CEA.

4. A hybridoma which produces a monoclonal antibody that is specific to carcinoma orosomucoid-related antigen (CORA) glycoprotein,
   said antibody having substantially no cross-reactivity with alpha-1-acid (AGP), and
   said CORA glycoprotein having a binding affinity for the tumor marker CEA, having a molecular weight of about 46,000–50,000 daltons, an isoelectric point in the range of about 3.0–3.5, a carbohydrate content of about 30% by weight, of which approximately 10.3% is N-acetyl glucosamine and approximately 0.2% is fucose, and having substantially no cross-reactivity with antisera to NCA or to CEA.

5. The hyridoma of claim 4 wherein said hybridoma is a fusion product of a mouse myeloma cell and a spleen cell from a mouse previously immunized with slow clearing CEA.

6. The hybridoma of claim 4 wherein said myeloma cells comprise cells from NS-1 cell line.

7. The hybridoma of claim 4 wherein said mouse had previously been immunized with the CORA glycoprotein.

8. A device for assay or purification purposes, said device comprising:
   (a) a support; and
   (b) at least the Fab portion of said monoclonal antibody of claim 2 bound to said support.

9. A method of detecting a carcinoma cell that synthesizes CEA comprising the steps of:
   (a) contacting a biological sample with an antibody or the Fab fragment thereof which is specific to carcinoma orosomucoid-related antigen (CORA) glycoprotein but which has substantially no cross-reactivity with alpha-1-acid (AGP),
   said CORA glycoprotein having a binding affinity for the tumor marker CEA, having a molecular weight of about 46,000–50,000 daltons, an isoelectric point in the range of about 3.0–3.5, a carbohydrate content of about 30% by weight, of which approximately 10.3% is N-acetyl glucosamine and approximately 0.2% is fucose, having reactivity with a monoclonal antibody raised thereto, and having substantially no cross-reactivity with antisera to NCA or to CEA; and
   (b) observing whether said antibody reacts with said sample, a reaction being indicative of the presence of said CEA-synthesizing carcinoma cell.

10. The method of claim 9 wherein said antibody comprises a monoclonal antibody or the Fab fragment thereof which is specific to said CORA glycoprotein.

11. The method of claim 9 wherein said sample comprises biological material selected from a group consisting of whole blood, serum, ascites fluid, and a tissue biopsy, tissue culture, and in vitro histological preparations thereof.

12. A method of detecting and monitoring a patient for colorectal adenocarcinoma comprising the steps of:
   (a) subjecting a biological sample to a test indicating the presence of a cancer marker carcinoma orosumucoid-related antigen (CORA) glycoprotein,
   said CORA glycoprotein having a binding affinity for the tumor marker CEA, having a molecular weight of about 46,000–50,000 daltons, an isoelectric point in the range of about 3.0–3.5, a carbohydrate content of about 30% by weight, of which approximately 10.3% is N-acetyl glucosamine and approximately 0.2% is focuse, having reactivity with a monoclonal antibody raised thereto, and having substantially no cross-reactivity with antisera to NCA or to CEA; and
   (b) determining whether the CORA glycoprotein is present, the presence of said CORA glycoprotein being indicative of the presence of colorectal adenocarcinoma.

13. The method of claim 12 wherein said test comprises an immunoassay.

14. A kit for screening a patient for carcinoma, said kit comprising an antibody specific to carcinoma orosomucoid-related antigen (CORA) and further comprising an antibody specific to a carcinoma marker selected from the group consisting of CEA, CA 19.9, NCA and AGP.

15. The kit of claim 14 wherein said kit is useful for screening for colorectal adenocarcinoma.

* * * * *

UNITED STATES PATENT AND TRADEMARK OFFICE
CERTIFICATE OF CORRECTION

PATENT NO. : 4,914,021

DATED : 3 April 1990

INVENTOR(S) : Carol A. Toth and Peter Thomas

It is certified that error appears in the above-identified patent and that said Letters Patent is hereby corrected as shown below:

Col. 4, line 35, "antisera;" should be --antisera:--

Col. 5, line 63, "ELISA" should be --ELIZA--.

Col. 7, line 26, "ELISA" should be --ELIZA--.

Col. 7, line 27, "ELISA" should be --ELIZA--.

Col. 9, line 37, "rate" should be --rat--.

Col. 10, line 26, "ELISA" should be --ELIZA--.

Col. 11, line 13, after "alpha-1-acid" insert

--glycoprotein--.

Col. 11, line 42, after "alpha-1-acid" insert

--glycoprotein--.

Signed and Sealed this

Fourth Day of May, 1993

Attest:

MICHAEL K. KIRK

*Attesting Officer*  *Acting Commissioner of Patents and Trademarks*